Jan. 30, 1951 C. A. ELMER Plant Pat. 1,002
ROSE PLANT
Filed Feb. 7, 1950
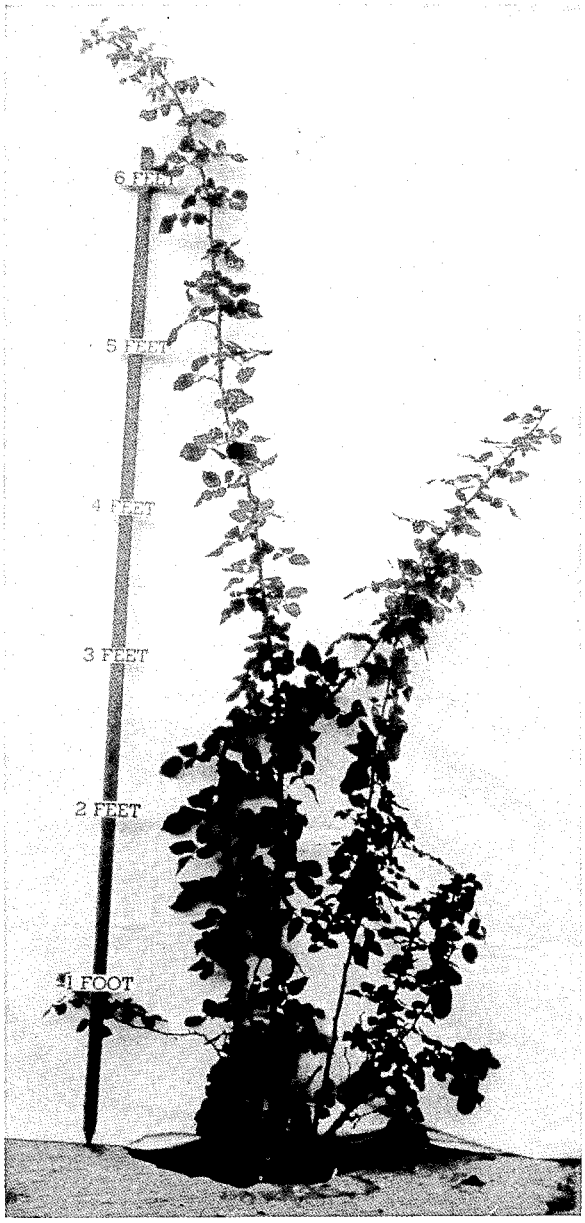
Inventor
Constance A. Elmer
By Robert Cobb
Attorneys Patented Jan. 30, 1951

Plant Pat. 1,002

UNITED STATES PATENT OFFICE 1,002

ROSE PLANT

Constance A. Elmer, San Gabriel, Calif., assignor to Germain's Inc., Van Nuys, Calif., a corporation of California Application February 7, 1950, Serial No. 142,794

1 Claim. (Cl. 47—61)

The present discovery relates to a new and distinct variety of rose plant, originating as a sport of the rose "Best Regards" (Plant Patent No. 652) and distinguishable therefrom dominantly by its climbing habit.

The parent plant is a bush rose of the hybrid tea class and is notable for the giant size and distinctive color of its flowers, and its profuse and continuous blooming habit.

Of importance here, however, is the fact that the new variety is extremely vigorous in growth, attaining a height of seven feet from April 5th planting to November 18th when the specimen in the accompanying drawing was depicted.

Aside from this climbing habit, the new variety is erect and branching, but otherwise has the same general characteristics that are present in its parent bush variety, having reference to its foliage, color, buds, flowers, etc. It is, therefore, unnecessary to describe the plant in detail, since it conforms to the description contained in the previously identified patent for the parent variety, excepting only as to the parent's habit of growth as a bush.

The new variety has been carefully tested ever since its discovery, and has been reproduced asexually by budding at San Gabriel, California, and the climbing characteristic noted appeared to be fully established and fixed, and transmitted to the progeny.

I claim:

A new and distinct variety of rose plant, having the same characteristics as its parent "Best Regards" (Plant Patent No. 652) in respect to its foliage, color and form of buds and flowers, but distinguished therefrom by its strong and vigorous climbing habit, and erect and branching growth, substantially as shown and described.

CONSTANCE A. ELMER.

No references cited.